US012676221B2

(12) United States Patent
Kokkinos et al.

(10) Patent No.: US 12,676,221 B2
(45) Date of Patent: Jul. 7, 2026

(54) SEMANTIC NETWORK FOR BIOACTIVE COMPOUND DISCOVERY FROM SCIENTIFIC LITERATURE

(71) Applicant: PIPA LLC, Davis, CA (US)

(72) Inventors: Yiannis Kokkinos, Athens (GR); Theodoros Panagiotakos, Athens (GR); Akis Nousias, Salonika (GR); Yiannis Makris, Athens (GR); Ilias Tagkopoulos, Davis, CA (US)

(73) Assignee: PIPA LLC, Davis, CA (US)

( * ) Notice: Subject to any disclaimer, the term of this patent is extended or adjusted under 35 U.S.C. 154(b) by 802 days.

(21) Appl. No.: 17/987,535

(22) Filed: Nov. 15, 2022

(65) Prior Publication Data

US 2023/0186114 A1     Jun. 15, 2023

Related U.S. Application Data

(60) Provisional application No. 63/280,532, filed on Nov. 17, 2021.

(51) Int. Cl.
| | |
|---|---|
| *G16H 20/00* | (2018.01) |
| *G06F 40/30* | (2020.01) |
| *G06N 5/022* | (2023.01) |
| *G16H 15/00* | (2018.01) |
| *G16H 70/00* | (2018.01) |

(52) U.S. Cl.
CPC ............. *G16H 20/00* (2018.01); *G06F 40/30* (2020.01); *G06N 5/022* (2013.01); *G16H 15/00* (2018.01); *G16H 70/00* (2018.01)

(58) Field of Classification Search
None
See application file for complete search history.

(56) References Cited

PUBLICATIONS

Tyagin et al., Interpretable Visualization of Scientific Hypotheses in Literature-based Discovery; bioRxiv preprint doi: https://doi.org/10.1101/2021.10.29.466471; Published Nov. 2, 2021; Total pp. 6 (Year: 2021).*

(Continued)

*Primary Examiner* — Alan Chen
(74) *Attorney, Agent, or Firm* — Run8 Patent Group, LLC; Peter Miller; Madison Tyrcha

(57) ABSTRACT

A method for automated therapy discovery includes: accessing a corpus of scientific publications; compiling a population of semantic concepts from the corpus of scientific publications into a vector space model; deriving domains of concepts in the vector space model based on proximity to domain descriptors in the vector space model; deriving association scores and action characteristics between connected concepts, based on proximity and action descriptors in the vector space model; generating a semantic network; receiving a query for a target concept and a target domain at a research portal; isolating a set of edges between a target node and a subset of nodes; identifying subsets of concepts along the set of edges; generating hypotheses for directions and magnitudes of effects of subsets of concepts on the target concept based on association scores and action characteristics stored in connections along the set of edges; and returning hypotheses to the research portal.

20 Claims, 4 Drawing Sheets

(56)  References Cited

PUBLICATIONS

Alachram et al., Text mining-based word representations for bio-medical data analysis and protein-protein interaction networks in machine learning tasks, Plos One | https://doi.org/10.1371/journal.pone.0258623; Published Oct. 15, 2021; Total pp. 20 (Year: 2021).*

Skrlj et al., PubMed-Scale Chemical Concept Embeddings Reconstruct Physical Protein Interaction Networks, Frontiers in Research Metrics and Analytics | www.frontiersin.org| vol. 6 | Article 644614; Published Apr. 2021; Total pp. 11 (Year: 2021).*

Yue et al., Graph embedding on biomedical networks: methods, applications and evaluations; Bioinformatics, 36(4), 2020, 1241-1251; Published Oct. 4, 2019; Total pp. 11 (Year: 2019).*

* cited by examiner

SEMANTIC NETWORK FOR BIOACTIVE COMPOUND DISCOVERY FROM SCIENTIFIC LITERATURE

CROSS-REFERENCE TO RELATED APPLICATIONS

This application claims the benefit of U.S. Provisional Application No. 63/280,532, filed on 17 Nov. 2021, which is incorporated in its entirety by this reference.

TECHNICAL FIELD

This invention relates generally to the field of bioinformatics and data science and more specifically to a new and useful method for automated therapy and bioactive discovery and for automated therapy and bioactive delivery in the field of bioinformatics and data science.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1A:
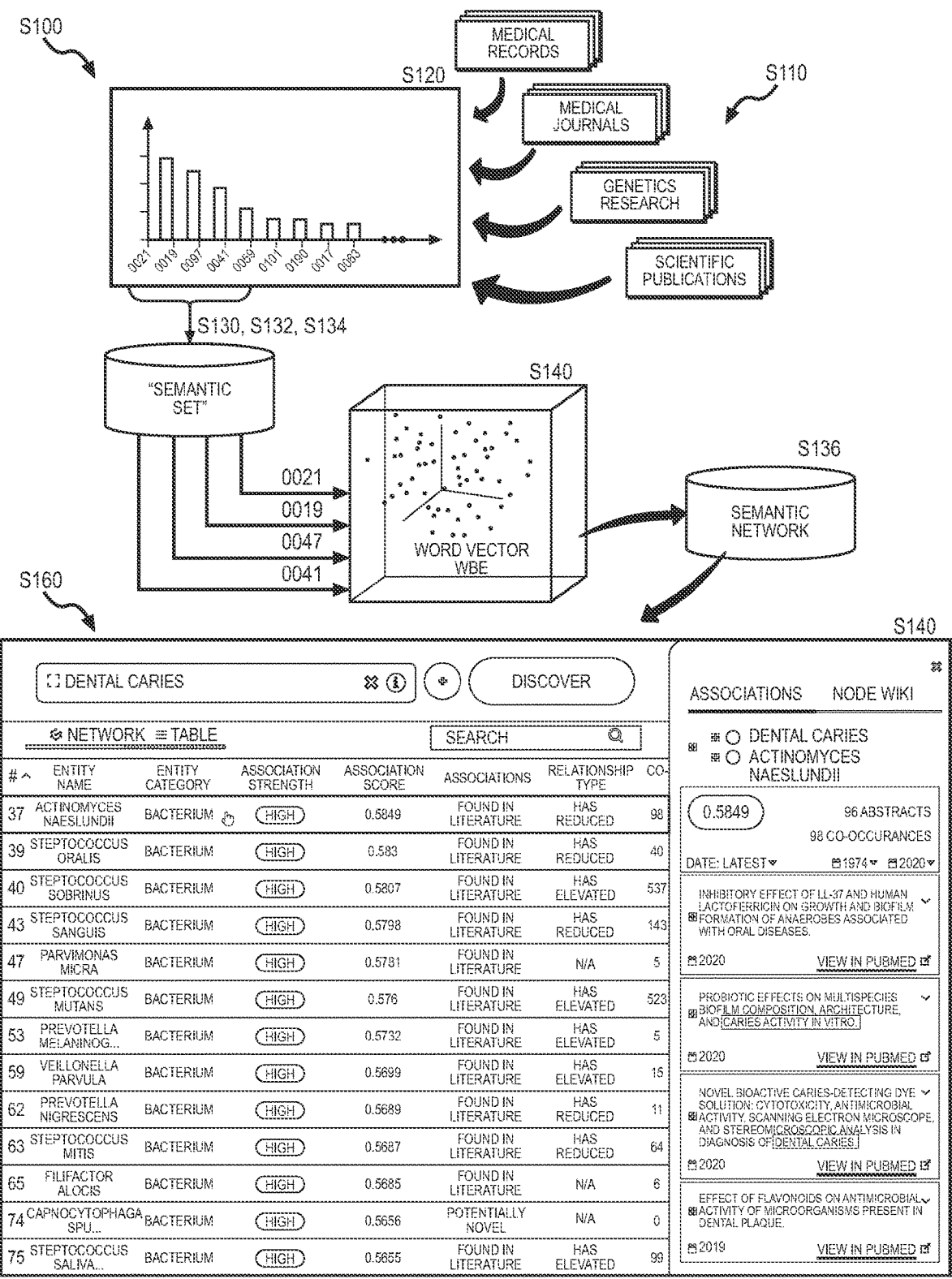
FIGS. 1A and 1B are a flowchart representation of a method.
Figure 1B:
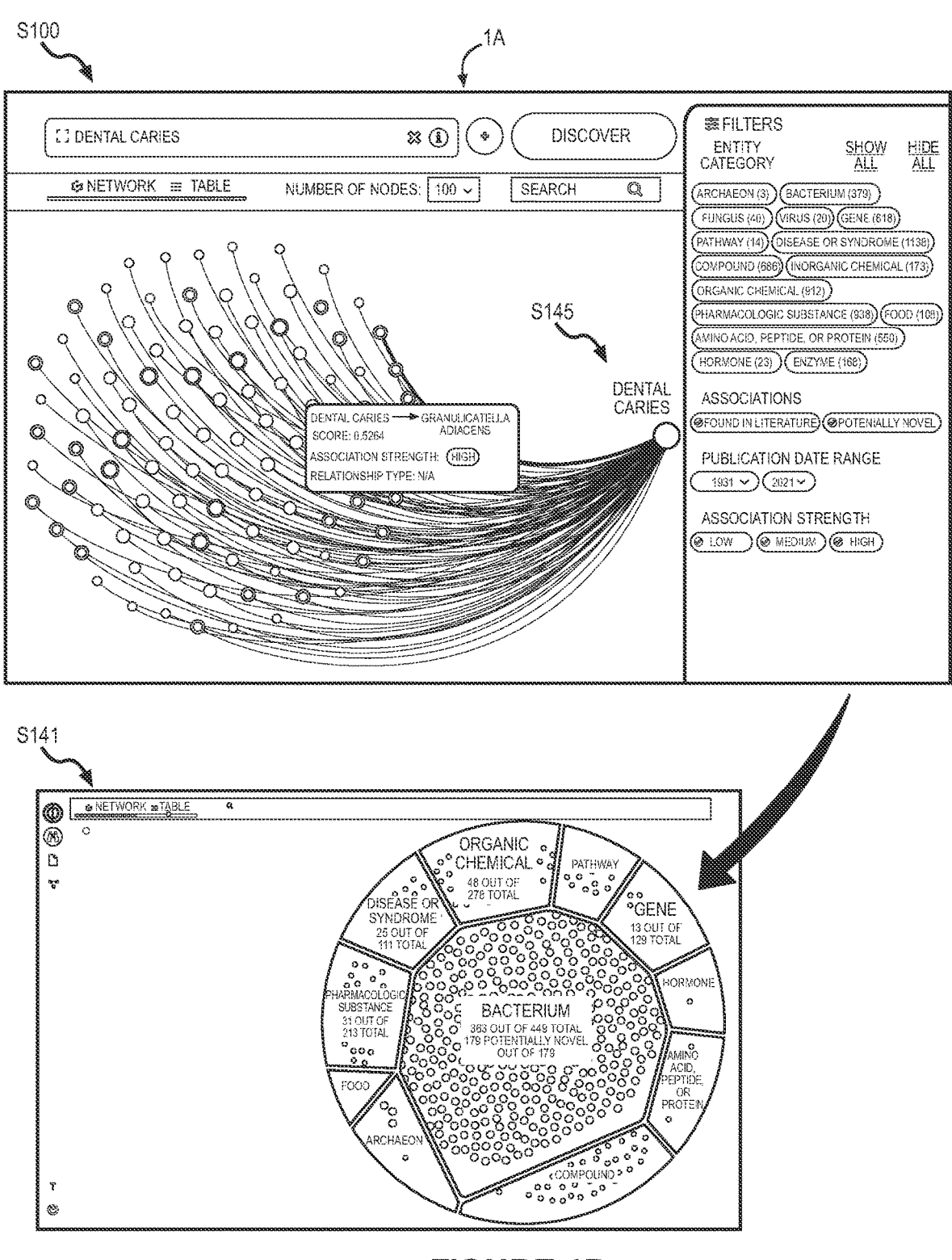

As shown in FIGS. 1A and 1B, a method S100 for automated therapy discovery includes: accessing a corpus of scientific publications in Block S110; compiling a population of semantic concepts represented in the corpus of scientific publications into a vector space model based on proximity of semantic concepts within individual scientific publications, in the set of scientific publications, and frequency of semantic concepts across the corpus of scientific publications in Block S120; deriving domains of a set of chemical and biological concepts in the vector space model based on proximity to domain descriptors in the vector space model in Block S130; deriving association scores between connected chemical and biological concepts, in the set of chemical and biological concepts, based on proximity in the vector space model in Block S132; deriving action characteristics between connected chemical and biological concepts, in the set of chemical and biological concepts, based on action descriptors in the vector space model in Block S134; generating a semantic network including a set of nodes representing the set of chemical and biological concepts and labeled with domains and including connections between nodes storing association scores and action characteristics in Block S136; and receiving a query for a target concept and a target domain at a research portal in Block S140. The method S100 further includes generating a set of hypotheses by: isolating a set of edges, in the semantic network, between a target node representing the target concept and a subset of nodes labeled with the target domain; for each edge in the set of edges in the semantic network, identifying a subset of chemical and biological concepts along the edge in the semantic network and generating a hypothesis, in the set of hypotheses, for a direction and a magnitude of an effect of the subset of chemical and biological concepts on the target concept based on association scores and action characteristics stored in connections along the edge in Block S158; and returning the set of hypotheses, ranked by magnitude of effect, to the research portal in Block S160.

Figure 2:
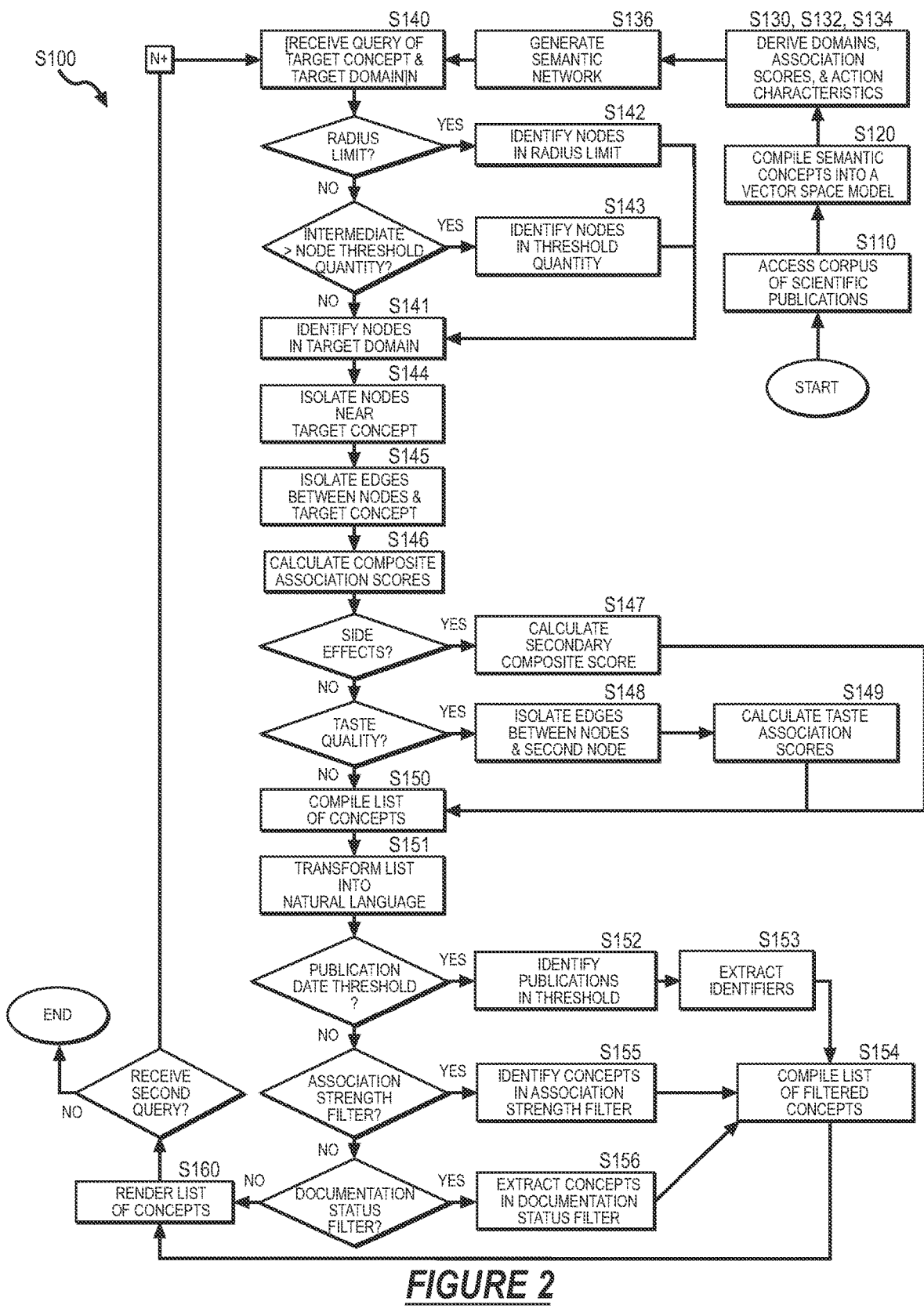
FIG. 2 is a flowchart representation of one variation of the method.

As shown in FIG. 2, one variation of the method S100 includes: accessing a corpus of scientific publications in Block S110; compiling a population of semantic concepts represented in the corpus of scientific publications into a vector space model in Block 120; deriving domains of a set of chemical and biological concepts in the vector space model based on proximity to domain descriptors in the vector space model in Block 130; deriving association scores between connected chemical and biological concepts, in the set of chemical and biological concepts, based on proximity in the vector space model in Block S132; deriving action characteristics between connected chemical and biological concepts, in the set of chemical and biological concepts, based on action descriptors in the vector space model in Block S134; generating a semantic network in Block S136; receiving a query for a target concept and a target domain at a research portal in Block S140; and identifying a target node representing the target concept and a subset of nodes labeled with the target domain in the semantic network in Block S141. The method S100 also includes generating a set of hypotheses by: identifying a subset of biological and chemical concepts in the target domain nearest the target concept and for each concept in the subset of biological and chemical concept, isolating a set of edges coupling the concept to the target concept; calculating a composite association score between the concept and the target concept based on a combination of association scores and directions contained in the set of edges in Block S146; and generating a hypothesis, in a set of hypotheses, for a direction and a magnitude of an effect of the concept on the target concept based on association scores and action characteristics stored in connections along the set of edges in Block S158. The method S100 further includes rendering a first list of concepts, ranked by association score, and linked to the set of hypotheses, for presentation within the research portal for the user in Block S160.

The method S100 further includes: accessing a corpus of scientific publications in Block S110; compiling a population of semantic concepts represented in the corpus of scientific publications into a vector space model based on proximity of semantic concepts within individual scientific publications, in the corpus of scientific publications, and frequency of semantic concepts across the corpus of scientific publications in Block S120; deriving domains of a set of concepts in the vector space model based on proximity to domain descriptors in the vector space model in Block S130; deriving association scores between connected concepts, in the set of concepts, based on proximity in the vector space model in Block S132; deriving action characteristics between connected concepts, in the set of concepts, based on action descriptors in the vector space model in Block S134; generating a semantic network in Block S136; receiving a query for a target concept and a target domain at a research portal in Block S140; isolating a set of edges, in the semantic network, between a target node representing the target concept and a subset of nodes labeled with the target domain in Block S141; identifying a subset of concepts along each edge of the set of edges in the semantic network; generating a hypothesis, in a set of hypotheses, for a direction and a magnitude of an effect of the subset of concepts on the target concept based on association scores and action characteristics stored in connections along each edge of the set of edges in Block S158; and returning the set of hypotheses, ranked by magnitude of effect, to the research portal in Block S160.

Figure 3:
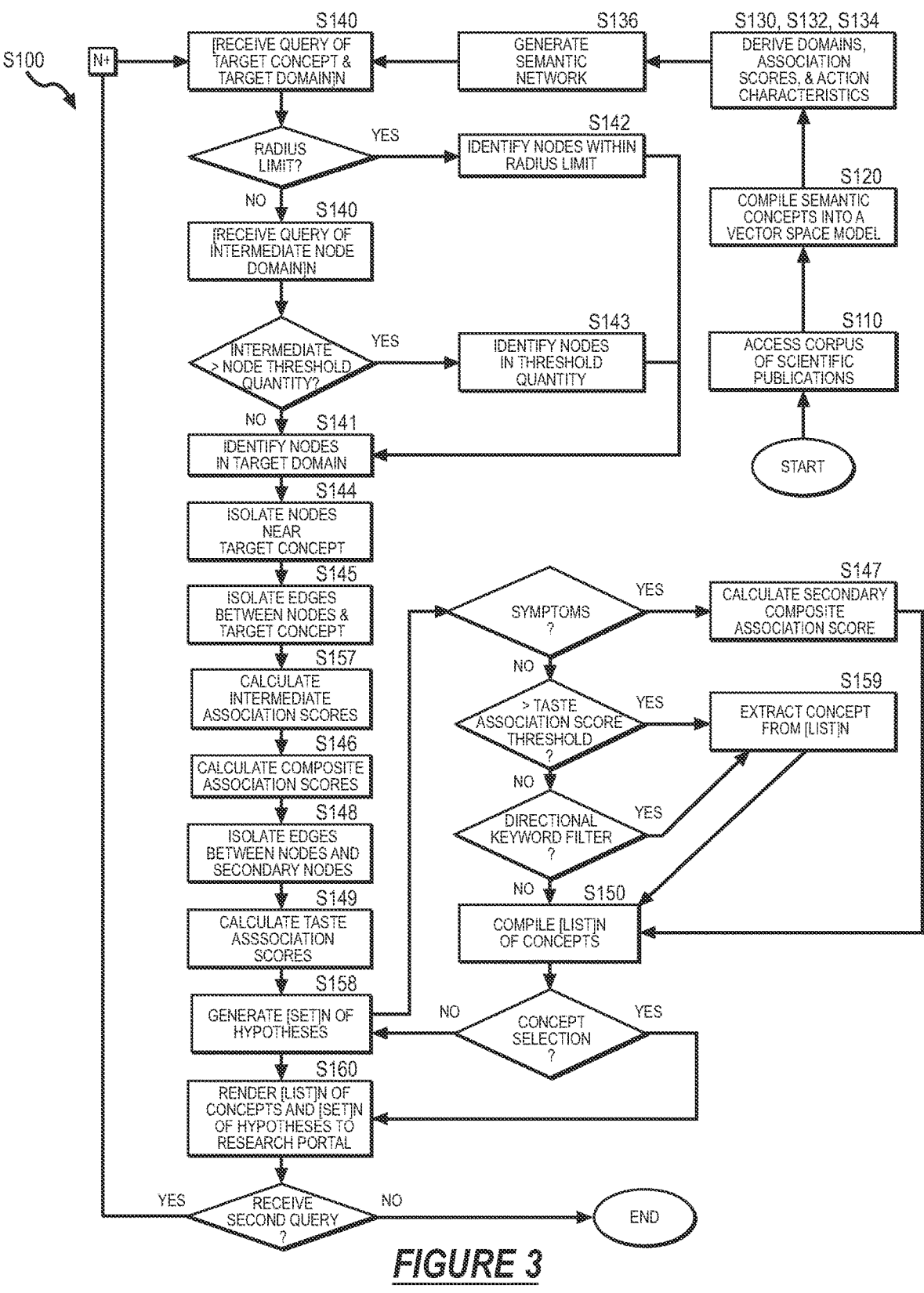
FIG. 3 is a flowchart representation of one variation of the method.

As shown in FIG. 3, one variation of the method S100 includes: accessing a corpus of scientific publications in Block S110; compiling a population of semantic concepts represented in the corpus of scientific publications into a vector space model in Block S120; deriving domains of a set of chemical and biological concepts in the vector space model based on proximity to domain descriptors in the vector space model in Block S130; and deriving association scores and action characteristics between connected chemical and biological concepts, in the set of chemical and biological concepts, based on proximity and action descriptors in the vector space model in Blocks S132, and S134. This variation of the method S100 further includes generating a semantic network including a set of nodes representing the set of chemical and biological concepts labeled with domains and connections between nodes storing association scores and action characteristics in Block S136. This variation of the method S100 also includes: receiving a query for a target concept and a target domain at a research portal in Block S140 and generating a set of hypotheses by isolating an initial set of edges, in the semantic network, between a target node representing the target concept and a subset of nodes labeled with the target domain in Block S141; then, for each node in the subset of nodes, labeled with the target domain, isolating a first set of edges coupling the node to the target concept in Block S145; calculating a composite association score between the target concept and the node in Block S146; isolating a second set of edges coupling the node to a nearest secondary node, in the semantic network, labeled with a taste quality in Block S148; calculating a taste association score between the taste quality and the node in Block S149; generating a hypothesis, in a set of hypotheses, for a direction and a magnitude of an effect of the taste quality on the target concept based on association scores and action characteristics stored in connections along the first set of edges in Block S158; and returning the set of hypotheses, ranked by magnitude of effect, to the research portal in Block S160.

Another variation of the method S100 includes generating a semantic network including: a set of nodes representing a set of chemical and biological concepts labeled with domains; and connections between nodes storing association scores and action characteristics in Block S136. This variation of the method S100 further includes receiving a query for a target concept and a target domain at a research portal in Block S140, and generating a set of hypotheses by: isolating a first set of edges, in the semantic network, between a target node representing the target concept and a set of nodes labeled with the target domain in Block S145; for each edge in the first set of edges, calculating an intermediate association score, in a first set of intermediate association scores, based on association scores and directions contained in connections between intermediate nodes along the edge in the semantic network in Block S157; and calculating a first set of composite association scores between the target node and the set of nodes labeled with the target domain, based on a first combination of the first set of intermediate association scores in Block S146. This variation of the method S100 also includes: isolating a second set of edges between intermediate nodes along the first set of edges to a set of nearest secondary nodes, in the semantic network, labeled with taste qualities in Block S148; for each edge in the second set of edges, calculating a taste association score between the taste quality and the intermediate node based on a second combination of association scores and action characteristics contained in connections along the edge in Block S149; generating a hypothesis, in a set of hypotheses, for a direction and a magnitude of an effect of the taste quality on the target concept based on association scores and directions stored in connections along the edge in Block S158; and returning the set of hypotheses, ranked by magnitude of effect, to the research portal in Block S160.

Another variation of the method S100 includes generating a semantic network which includes: a set of nodes representing a set of chemical and biological concepts extracted from a corpus of scientific publications and labeled with domains; and connections between nodes storing association scores and action characteristics in Block S136. This variation of the method S100 further includes receiving a query for a target concept and a target domain at a research portal in Block S140 and generating a set of hypotheses by isolating an initial set of edges, in the semantic network, between a target node representing the target concept and a subset of nodes labeled with the target domain in Block S145. This variation of the method S100 also includes, for each node in the subset of nodes, labeled with the target domain: isolating a first set of edges coupling the node to the target concept; calculating a composite association score between the target concept and the node based on a combination of association scores and directions contained in the first set of edges in Block S146; isolating a second set of edges coupling the node to a nearest secondary node, in the semantic network, labeled with a taste quality in Block S148; calculating a taste association score between the taste quality and the node based on a second combination of association scores and directions contained in the second set of edges in Block S149; generating a hypothesis, in a set of hypotheses, for a direction and a magnitude of an effect of the taste quality on the target concept based on taste association scores and action characteristics stored in connections along the second set of edges in Block S158; and returning the set of hypotheses, ranked by magnitude of effect, to the research portal in Block S160.

2. Applications

Generally, the method S100 can be executed by a computer system (e.g., a computer network, a remote computer system) to: derive associations between language concepts (e.g., chemical compounds, bioactive compounds, genes, diseases, microbes, taste qualities) based on proximities of these concepts across a corpus of resources (e.g., scientific journals, medical records); derive directional effects (or "action pathways") between associated language concepts based on action descriptors in the corpus of resources; derive domains or concept types of these language concepts based on domain descriptors in the corpus of resources; and represent these language concepts, the strengths and action pathways between these language concepts, and the domains of these language concepts in a semantic network.

The computer system can further execute Blocks of the method S100 to: receive search terms (e.g., a disease, a pathway type, a therapy type) from a user via a user portal; query the knowledge graph for edges (e.g., combinations of nodes and connections) that connect nodes that represent these search terms; generate hypotheses for whether, how, and to what extent actions (e.g., pharmaceutical therapies, chemical compounds, taste qualities) may affect these search terms; and return these hypotheses to the user via the user portal.

The user may then selectively target or prioritize research and development of certain therapies based on these hypotheses.

Therefore, the computer system can execute Blocks of the method S100 to streamline research and development of chemical compounds and other therapies for humans (and other animals). For example, the computer system can execute Blocks of the method S100 to identify and propose new applications of existing compounds to address a target disease; or known applications of existing compounds (and/or microbes, genes, gene therapies, etc.) to address a target disease through novel action pathways.

In particular, the computer system: compiles many (e.g., millions) journals, scientific publications, medical records, gene sequences, blood panels, microbiome panels, and/or resources; automatically derives domains, strengths of associations and directions of action pathways between many chemical and biological concepts described across these resources—whether in titles, abstracts, bodies, or footnotes of these resources; and represents the chemical and biological concepts, strengths of associations, and directions of action pathways in edges within a semantic network. Accordingly, the computer system can return immediate and meaningful hypotheses for targeted research and development of therapies given minimal search terms, such as merely: a single disease descriptor and a therapy type (e.g., chemical compound or medical treatment); or a single disease descriptor and a pathway type (e.g., bacteria, gene).

3. Terms

Generally, the semantic network (e.g., knowledge graph, ontology) includes nodes representing biological and chemical concepts labeled with domains and connections between nodes storing association scores and action characteristics.

More specifically, a biological and chemical concept (e.g., a gene sequence, a disease, a microbe, a bioactive compound, a taste quality, a food product) can be represented in nodes containing biological and chemical concepts. Domains in the semantic network can include diseases, compounds, genes, bacterium, fungi, taste perception, etc. Taste perception can include taste qualities (e.g., bitterness, sweetness, saltiness, sourness, umami taste) that are connected to taste chemicals (e.g., tastants) of consumable substances (e.g., food, beverages) informed by a corpus of scientific resources. Association scores can be stored in connections between nodes along edges in the semantic network and represent strengths of correlations between two concepts based on proximity in the word vector cube and/or based on proximity of these two concepts in individual resources across the corpus of resources. The categories of association scores can include association scores, intermediate association scores, taste association scores, and composite association scores. Furthermore, composite association scores represent the average of association scores from a start node to a terminal node or the average intermediate association scores from a start node to an intermediate node or the average intermediate association scores from an intermediate node to a terminal node.

Similarly, action characteristics represent directions of correlations between connected chemical and biological concepts based on the presence of directional keywords between connected biological and chemical concepts within individual scientific publications of the corpus of scientific publications. More specifically, directional keywords can be divided into two categories: positive actions (e.g., upregulates, catalyzes, starts, causes, promotes, grows, induces) and negative actions (e.g., downregulates, inhibits, stops, prevents, demotes, kills, reduces).

Furthermore, a user can enter queries within a user portal (or "research portal") to verify hypotheses and to inform clinical, chemical, and/or biological research that addresses a target concept and a target domain within the semantic network.

3.1 Resources

Block S110 of the method recites accessing a corpus of scientific publications. Generally, in Block S110, the computer system can retrieve scientific papers and journal publications, (anonymized) patient health records, genetic data, microbiome data, gustatory sensation data, taste perception data, sensory perception data, and/or medical histories, etc. from one or more resource databases.

4. Word Vector Cube

Block S120 of the method recites compiling a population of semantic concepts represented in the corpus of scientific publications into a vector space model based on proximity of semantic concepts within individual scientific publications, in the set of scientific publications, and frequency of semantic concepts across the corpus of scientific publications. Generally, in Block S120, the computer system can construct a vector space model (e.g., a "word vector cube") that represents (or "embeds") word representations from the corpus of resources in a continuous vector space where semantically-related word representations are mapped to nearby points in the vector space—that is, semantically-related word representations are "embedded" nearby each other in the vector space.

More specifically in Block S120, the computer system can generate a multi-dimensional word vector cube that contains a large population of chemical and biological concepts mapped according to semantic proximity derived from the corpus of resources. Each object in the word vector cube: can include a word or phrase representing a chemical or biological concept (e.g., a gene sequence, a disease, a microbe); and can be located at a "distance" (e.g., a multi-dimensional spatial distance, a weight, a proximity value) to another object in the word vector cube corresponding to a frequency that words or phrases represented by these two objects occur together in individual resources in the corpus.

4.2 Vector Space Modeling

In one implementation, the computer system: accesses documents from a corpus of resources; detects and discards stop words (e.g., 'a', 'the', 'ourselves', 'hers', 'between', 'yourself', 'but', 'again', 'there', 'about', 'once', 'out') from each document; and initiates generation of the word vector cube based on the remaining words in these documents. The computer system can then implement statistical methods to identify a unique combination of words occurring in each document in this corpus of resources, such as a unique combination of five words or a quantity of words proportional to a length of a document. For example, to identify a unique combination of words in one document in the corpus of resources, the remote computer system can: detect and remove all stop words from the document; convert all plurals of words in the document to their singular forms; implement statistical methods to identify a target quantity of words occurring with greatest frequency in the document; and store these words as a combination of words tagged with a topic label extracted from this document. The remote computer system can repeat this process for each other document in the corpus of resources to generate a population of topic words tagged with topics represented across the corpus of resources.

The computer system can then implement vector space modeling techniques to aggregate this population of objects into a multi-dimensional word vector cube with many nodes—each containing one object in the population—related spatially based on proximity of corresponding topic words occurring throughout the corpus of resources.

4.3 Concepts

Generally, the corpus of resources may describe a range of concepts (and directly or indirectly inform relationships between these concepts) in various domains, such as: genes; compounds, pharmacologic substances, inorganic chemicals, and/or organic chemicals; proteins, peptides, and/or amino acids; hormones; enzymes; diseases, syndromes, and/or and disease stages; symptoms and symptom magnitudes; microbes (e.g., bacteria, viruses, fungi); sample population characteristics (e.g., age or age group, gender, geographic location, medical histories, diagnoses, symptoms, treatments, genetic information, blood test results, microbiome panel); treatment or experiment actions (e.g., dose size, administration time windows, administration types); etc.

Accordingly, the computer system can implement the foregoing methods and techniques to extract concepts within these domains from the corpus of resources, to characterize their proximities in these documents and across the corpus of resources, and to represent these proximities within a word vector cube or other vector space model.

5. Semantic Network

Block S136 of the method recites generating a semantic network (e.g., knowledge graph, ontology): including a set of nodes representing the set of chemical and biological concepts and labeled with domains; and including connections between nodes storing association scores and action characteristics. Generally, in Block S136, the computer system can generate a knowledge graph that represents proximities (or "associations") of concepts in the word vector cube, domains of these concepts, and action characteristics (e.g., action directions, correlation direction) between these concepts informed by the corpus of resources.

5.1 Association Score

In one implementation, the computer system interprets strengths of associations (or "association scores") between two concepts based on proximity of these concepts within the word vector cube—that is, inversely proportional to an n-dimensional distance between these two concepts in the word vector cube.

In another implementation, for two concepts (e.g., two words or two phrases) represented in the word vector cube, the computer system can calculate an association score:

proportional to a number of times (or "frequency") that two concepts appear within the same resource (e.g., within the title, abstract, body, and/or footnotes of the resource); inversely proportional to a distance (e.g., a number of letters or words) between paired instances of these two concepts in the resource; and/or proportional to a number of resources in the corpus of resources that includes at least one instance of each of these two concepts.

Accordingly, the computer system can represent strengths of correlations between two concepts based on proximity in the word vector cube and/or based on proximity of these two concepts in individual resources across the corpus of resources.

5.2 Concept Domain

In one implementation, the computer system also predicts domains of concepts represented in the word vector cube and/or filters concepts represented in the word vector cube to include a particular set of relevant (or "target") domains, such as: genetic information; compounds, pharmacologic substances, inorganic chemicals, and/or organic chemicals; proteins, peptides, and/or amino acids; hormones; enzymes; diseases, syndromes, and/or and disease stages; symptoms; bacteria; viruses; fungi; taste qualities; food products; waste products; patient population characteristics; and/or treatment or experiment actions.

For example, the computer system can: apply standard naming conventions for genes or genetic sequences to identify particular words or phrases in the word vector cube as genes and genetic sequences in the semantic network; apply standard naming conventions for compounds and chemical formulae to identify particular words or phrases in the word vector cube as chemical compounds in the semantic network; apply standard naming conventions for diseases and diagnoses to identify particular words or phrases in the word vector cube as diseases in the semantic network; apply standard naming conventions for therapy administration and experiment actions and diagnoses to identify particular words or phrases in the word vector cube as pathway or experiment actions in the semantic network; and label concepts in the semantic network with their domains accordingly.

Additionally or alternatively, the computer system can: detect domain descriptors in the word vector cube; and identify or predict the domain of a particular concept (i.e., a word or phrase) in the word vector cube based on a domain descriptor nearest this concept in the word vector cube. For example, the computer system can identify a concept in the word vector cube as "bacterium" if an association score between the concept and other objects—identified as [bacteria, bacterium, organism, prokaryotic, and/or microorganism] domain descriptors in the word vector cube—are high. More specifically, the computer system can identify a concept in the word vector cube as "bacterium" if a combination (e.g., sum) of the association scores between the concept and known bacteria-related language descriptors (e.g., bacteria, bacterium, organism, prokaryotic, and/or microorganism) exceeds a threshold score.

5.3 Action Characteristics

Furthermore, the computer system can derive an action characteristic (or "pathogen score") representing positive or negative correlation between two concepts (e.g., in the same or different domains) based on affirmative and negative language contained in the corpus of resources and/or represented in the word vector cube.

In one implementation, the computer system calculates action characteristics between −1.000 and +1.000. In particular, for two concepts represented in the word vector cube, the computer system can calculate a negative action component: proportional to a number of times (or "frequency") that the two concepts appear within the same resource with negative language (e.g., "not," "inhibits", "down-regulates", "reverse," "mitigate," "reduce," "attenuate") surrounding or arranged between these two concepts; inversely proportional to the distance (e.g., number of letters or words) between these two concepts and negative language in the resource; and proportional to a number of resources that includes both concepts with interstitial negative language. The computer system can similarly calculate positive an action component for the two concepts: proportional to a number of times that two concepts appear within the same resource without negative language or with positive language (e.g., "increase," "up-regulated", "activate", "enforce," "augment") between the two concepts; inversely proportional to the distance (e.g., number of letters or words) between these two concepts with no negative language and/or with positive language therebetween in the resource; and proportional to a number of resources that includes both concepts with no interstitial negative language and/or with no interstitial positive language. The computer system can then combine (e.g., sum, average) the negative and positive action component to derive a (composite) action characteristic between the two concepts.

For example, the word vector cube can represent a high association score and a positive action characteristic between a first concept in a disease domain and a second concept in a gene domain. Accordingly, in this example, the first and second concepts may be frequently described together in individual resources in the corpus of resources; and presence of the disease and presence of the gene may be strongly correlated, which may indicate that the gene predicts presentation of the disease and/or the disease activates expression of the gene.

In another example, the word vector cube represents a high association score and a negative action characteristic between a first concept in the disease domain and a second concept in the bacterium domain. Accordingly, in this example, the first and second concepts are frequently described together in individual resources; and absence or mitigation of the disease and presence of the bacteria may be strongly correlated, which may indicate that the bacteria offer resistance to the disease and/or the bacteria is a prophylactic treatment for the disease.

In yet another example, the word vector cube represents a high association score and a neutral action characteristic between a first concept in the bacterium domain and a second concept in compound domain. Accordingly, in this example, the first and second concepts are frequently described together in individual resources; but the corpus of resources are silent to or fail to return consensus on effects of the compound on the growth of presence of the bacteria—or vice versa.

5.4 Semantic Network Construction

The computer system can then: populate a semantic network (or "semantic network") with a constellation of nodes, each representing a unique concept—in the set of target domains—described in at least one resource in the corpus of resources; label each node with its corresponding domain; define connections between nodes in the semantic network; label each connection with an association score for the two concepts represented by the nodes its connects; and/or label each connection with an action characteristic derived from the word vector cube and/or interpreted directly from the corpus of resources into a semantic network.

The computer system can then: populate a semantic network with a constellation of nodes, each representing a unique concept—in the set of target domains—described in at least one resource in the corpus of resources; label each node with its corresponding domain; define connections between nodes in the semantic network; label each connection with an association score for the two concepts represented by the nodes its connects; and/or label each connection with an action characteristic derived from the word vector cube and/or interpreted directly from the corpus of resources into a semantic network.

Furthermore, the computer system can: project sets of edges, in the semantic network, between the target node and a subset of nodes onto a virtual surface to generate a visualization of a region of the semantic network representing connections between a target concept and a target domain; label edges, represented in the visualization, with concepts extracted from nodes between the target node and the subset of nodes in the semantic network; and render the visualization within the research portal.

Additionally or alternatively, the computer system can project sets of edges, in the semantic network, between the target node, intermediate nodes, and the subset of nodes onto a virtual surface to generate a visualization of a region of the semantic network representing connections between the target concept, taste qualities, and the target domain.

Therefore, the computer system can generate a visualization of the entire semantic network or a selected region of the semantic network for user interaction within the research portal.

5.5 Resource Callback

In one variation, the computer system also writes identifiers of resources that informed connections between nodes in the semantic network to these connections.

For example, for a connection between a first node containing a first concept and a second node containing a second concept, the computer system can: retrieve an identification number (e.g., "ISBN," "ISSN," or "DOI"), web address, or other unique identifier for each paper that contains both the first and second concepts; define an unique identifier to each medical record that contains both the first and second concepts; and write these identifiers to the connection between the first and second nodes. Later, the computer system can extract these identifiers from the semantic network, retrieve a set of resources based on these identifiers, and present these resources to the user to support a system-generated hypothesis when a user selects an edge intersecting this connection.

6. User Query

Block S140 recites receiving a query for a target concept and a target domain.

Generally, in Block S140, the computer system interfaces with a research portal (or "user portal") to receive a set of natural language search terms entered by a user, such as one or more of: a particular gene or generic gene domain term; a particular compound, pharmacologic substance, inorganic chemical, organic chemical, or generic compound domain term; a particular protein, peptide, and/or amino acid or a generic protein domain term; a particular hormone or a generic hormone domain term; a particular enzyme or a generic enzyme domain term; a particular disease, syndrome, and/or disease stage or a generic disease domain term; a particular symptom or a generic symptom domain term; a particular bacterium or a generic bacteria domain term; a particular virus or a generic virus domain term; a particular fungus or a generic fungi domain term; a particular waste product or a generic waste product domain term; a particular food product or a generic food product domain term; a particular taste quality or a generic taste quality domain term; a particular patient population characteristic or a generic patient characteristic domain term; or a particular pathway or experiment action or a generic treatment domain term.

Additionally or alternatively, the computer system interfaces with the research portal to receive selections of various filters and/or thresholds (e.g., association strength, publication date range, association score, documentation status, directional keywords) entered by the user.

7. Discovery

Then, in response to receipt of a set of search terms, the computer system can: query the semantic network for concepts and domains that match or approximate these search terms; and return a list of these matched concepts, association scores between these concepts, and action characteristics between these concepts in Block S160.

Accordingly, the computer system can present concepts (e.g., diseases, bacterium, and compounds; symptoms, genetics, compounds) that fulfill the user's search terms, that are directly connected (e.g., found in literature) or indirectly connected (e.g., found in medical records rather than peer-reviewed literature) in the semantic network, and that are predicted to exhibit correlation within a population.

Additionally or alternatively, after the computer system presents concepts that fulfill the user's search terms, in response to selection of a filter (or "threshold") (e.g., association strength, publication date range, association score, documentation status, directional keyword filter) at the research portal, the computer system can: query the semantic network for concepts and domains that match or approximate the search terms according to the filter; return a list of these matched concepts ranked by association scores, publication dates, documentation status, association strength, and/or directional keywords according to the selected filter; and sort a previously generated list of concepts according to the selected filter.

For example, in response to selection of a high association strength filter at the research portal, the computer system can: access a first definition of high association strength; identify a first subset of compound concepts, from the first list of compound concepts, exhibiting high association strength based on the first definition of high association strength in Block S155; compile the first subset of compound concepts into a second list of compound concepts ranked by composite association score and labeled with high association strength in Block S154; and render the second list of compound concepts within the research portal for the user in Block S160.

In another example, in response to selection of a direct documentation status filter at the research portal, the computer system can: extract a first subset of biological and chemical concepts from a list of biological and chemical concepts, exhibiting a direct documentation status in Block S156; compile the first subset of biological and chemical concepts into a second list of biological and chemical concepts according to the direct documentation status filter in Block S154; and render the second list of biological and chemical concepts, labeled with direct documentation statuses, within the research portal for the user to review in Block S160.

In yet another example, in response to selection of a first publication date threshold from the research portal, the computer system can: identify a first subset of scientific publications in the corpus of scientific publications exhibiting publication dates occurring after the first publication date threshold in Block S152; and extract a first cluster of identifiers from the semantic network corresponding to the first subset of scientific publications and the second subset of scientific publications in Block S153. Then, in response to selection of a second publication date threshold from the research portal, the computer system can: identify a second subset of scientific publications in the corpus of scientific publications exhibiting publication dates occurring before the second publication date threshold in Block S152; extract a second cluster of identifiers from the semantic network corresponding to the second subset of scientific publications in Block S153; compile a list of a population of concepts represented in the first subset of scientific publications exhibiting publication dates occurring after the first publication date threshold and the second subset of scientific publications exhibiting publication dates occurring before the second publication date threshold in Block S154; and present the list of the population of concepts, labeled with the first cluster of identifiers and the second cluster of identifiers, within the research portal for the user in Block S160.

In yet another example, the computer system can execute Blocks of the method S100 to compile a first list of taste qualities, ranked by magnitude of effect and labeled with directional keywords; and render the first list of taste qualities for presentation within the research portal to the user. Then, in response to receiving selection of a directional keyword filter at the research portal, the computer system can: extract a subset of taste qualities, labeled with directional keywords, from the first list of taste qualities, based on the directional keyword filter; compile the subset of taste qualities into a second list of taste qualities, ranked by directional keywords; and render the second list of taste qualities within the research portal to the user.

7.1 Example: Multi-Step Compound Discovery

In one example shown in FIGS. 1A and 1B, the computer system assists a user developing a chewing gum that reduces dental caries by guiding the user toward: identifying a first set of pathogenic microbes in the mouth that promote dental caries; identifying a first set of compounds that suppress pathogenic microbes; identifying a second set of beneficial microbes in the mouth that prevent dental caries; identifying a second set of compounds that support beneficial microbes; and selecting from the first and second sets of compounds for development and trial.

Accordingly, the user enters a query that includes "dental caries AND bacteria" into a user portal supported by the computer system. The computer system then queries these terms against the semantic network, such as by scanning the semantic network for nodes labeled with "bacteria" or "dental caries" (or analogous) domains; and the semantic network returns a first set of node addresses of a population of nodes labeled with the "bacterium" domain but no hits for "dental caries."

The computer system then scans the semantic network for nodes containing a "dental caries" (or an analogous) concept; and the semantic network returns a node address of a particular node containing the "dental caries" concept. The computer system queries the semantic network for association scores and action characteristics stored in connections between the particular "dental caries" node and the first set of "bacteria" nodes; and the semantic network returns association scores and action characteristics stored in these connections. The computer system then isolates a subset of "bacteria" nodes with the highest association scores, such as with association scores greater than a threshold association score of 0.40. The computer system then generates a first list of bacteria stored in this subset of bacteria nodes and presents this first list to the user via the user portal.

For example, in response to receiving selection for the target concept including a target disease at the research portal and receiving selection for the target domain including bacteria concepts at the research portal in Block S140, the computer system can: generating a set of hypotheses: isolate the set of edges, in the semantic network, between the target node representing the target disease and the subset of nodes labeled as bacteria concepts; for each node, in the subset of nodes, labeled with a bacterium concept: isolate a set of edges coupling the node to the target concept in Block S145; and calculate a composite association score between the bacterium concept and the target disease based on a combination of association scores and directions contained in the set of edges in Block S146. Then the computer system can: compile a first list of bacteria concepts, ranked by composite association score in Block S150; and render the first list of bacteria concepts for presentation within the research portal to the user in Block S160.

For example, in response to receiving selection for the target concept including a target disease at the research portal and receiving selection for the target domain including bacteria concepts at the research portal in Block S140, the computer system can: generate a set of hypotheses: isolate the set of edges, in the semantic network, between the target node representing the target disease and the subset of nodes labeled as bacteria concepts; for each node, in the subset of nodes, labeled with a bacterium concept: isolate a set of edges coupling the node to the target concept in Block S145; and calculate a composite association score between the bacterium concept and the target disease based on a combination of association scores and directions contained in the set of edges in Block S146. Then the computer system can: compile a first list of bacteria concepts, ranked by composite association score in Block S150; and render the first list of bacteria concepts for presentation within the research portal to the user in Block S160.

Furthermore, in this example, the user then selects a particular bacterium from the list to initiate a new search involving this bacterium. To find a particular compound that effects the particular bacterium, the user adds "compound" (and/or pharmacologic substance, inorganic chemical, and/or organic chemical) to the new search. Accordingly, the computer system queries these terms against the semantic network, such as by scanning the semantic network for nodes labeled with "compound" or the particular bacterium (or analogous) domains; the semantic network returns a second set of node addresses of a population of nodes labeled with the "compound" domain. The computer system then scans the semantic network for nodes containing a concept analogous to the particular bacterium; the semantic network returns a node address of a particular node containing the concept of the particular bacterium. The computer system queries the semantic network for association scores and action characteristics stored in connections between the particular node and the second set of "compound" nodes; the semantic network returns association scores and action characteristics stored in these connections. The computer system thus isolates a subset of "compound" nodes with the highest association scores, such as with association scores greater than the threshold association score of 0.40.

The computer system then generates a second list of compounds stored in this subset of bacteria nodes and presents this second list to the user via the user portal. Thus, the computer system populates a list of compounds that are most often described near references to the particular bacterium in the corpus of resources.

In this example, if the action characteristic between this particular bacterium and "dental caries" is positive, the computer system can: predict that the particular bacterium is pathogenic and promotes dental caries; and present this hypothesis to the user. Accordingly, the user may filter the second list of compounds to include only a subset of compounds connected to the particular bacterium via negative action characteristics.

Conversely, if the action characteristic between this particular bacterium and "dental caries" is negative, the computer system can predict that the particular bacterium is beneficial and reduces dental caries; and present this hypothesis to the user. Accordingly, the user may filter the second list of compounds to include only a subset of compounds connected to the particular bacterium via positive action characteristics.

The user may then select a particular compound or subset of compounds to develop and trial in a gum to reduce dental caries, such as compounds associated with highest (or lowest) action characteristics for the particular bacterium selected by the user.

During the foregoing process, the computer system can also: extract identifiers of resources (i.e., journals, papers, medical records)—that contain the "dental caries" and particular bacterium concepts and/or that contain particular bacterium and particular compound concepts—from corresponding connections in the semantic network; and return a list of identifiers of, links to, or digital copies of these resources to the user, thereby enabling the user to immediately and directly access resources that informed correlations—between dental caries, various bacterium, and various compounds—predicted by the semantic network. The user may then refine or confirm bacterium and/or compound selections accordingly.

8. Action Pathways

In one variation, the computer system further derives possible action pathways between concepts searched or selected by the user based on secondary concepts contained in intermediate nodes along edges in the semantic network extending between these nodes. Accordingly, the computer system can present these action pathways to the user, thereby enabling the user to gain further insight into how one of these concepts directly or indirectly affects the other.

8.1 Example: Single-Step, Multi-Pathway Compound Discovery

In an example similar to the example described above, the user enters a query that includes "dental caries AND compound" into the user portal. Accordingly, the computer system implements methods and techniques similar to those described above to retrieve a set of compounds connected to "dental caries" (e.g., characterized by direct or indirect association scores with "dental caries" greater than the threshold association score).

In particular, in the foregoing example, "bacterium" in the user's search query functions as a user-defined hypothesis for root cause and/or for a pathway for mitigating dental caries and therefore functions to focus discovery of compounds that may affect dental caries exclusively to bacterium-related pathways. Conversely, in this example, exclusion of the search term "bacterium" expands the user's search through the semantic network to include any pathway (e.g., bacteria, genetics, viruses, fungi) that may affect dental caries.

For example, the search term "dental caries" defines a start node in the semantic network, and the search term "compound" defines a domain of terminal nodes branching from the "dental caries" start node. The semantic network can include one or more intermediate nodes in different domains (e.g., bacterium, gene, virus, fungus) along graph edges between the "dental caries" start node and the "compound" terminal nodes, and these intermediate nodes and edges can represent pathways for compounds—represented by the terminal nodes—to affect dental caries. The computer system can receive selection for the target concept including a target disease at the research portal and receive selection for the target domain including compound concepts at the research portal in Block S140. Next the computer system can isolate a set of edges, in the semantic network, between the target node representing the target disease and a subset of nodes labeled as compound concepts and, for each node in the subset of nodes, labeled with a compound concept: isolate a first set of edges coupling the node to the target concept in Block S145; and calculate a composite association score between the compound concept and the target concept based on a combination of association scores and directions contained in the first set of edges in Block S146. Then the computer system can: compile a first list of compound concepts, ranked by composite association score in Block S150; and render the first list of compound concepts for presentation within the research portal to the user in Block S160.

For example, upon receipt of the target concept, "dental caries," and target domain, "compound," search terms, the computer system queries these terms against the semantic network, such as by scanning the semantic network for nodes labeled with "compound" or "dental caries" (or analogous) domains; and the semantic network returns a set of terminal node addresses of a population of nodes labeled with the "compound" domain but no hits for "dental caries." The computer system then scans the semantic network for nodes containing a "dental caries" (or an analogous) concept; and the semantic network returns a node address of a start node containing the "dental caries" concept. The computer system queries the semantic network for association scores and action characteristics stored in connections between the start "dental caries" node and the set of terminal "compound" node addresses nodes.

In one implementation, for a first terminal "compound" node representing a first compound, the computer system isolates a single, shortest, contiguous edge from the first terminal "compound" node to the start "dental caries" node in the semantic network, such as an edge containing a small quantity of intermediate nodes, fewer than a threshold quantity of intermediate nodes, between the first terminal "compound" node to the start "dental caries" node.

For example, the computer system can: isolate a set of edges in the semantic network connecting the target node to nodes, labeled with the target domain, separated by fewer than a threshold quantity of intermediate nodes in the semantic network in Block S143.

Alternatively, the computer system can identify a single, shortest, contiguous edge—between the first terminal "compound" node and the start "dental caries" node—that exhibits a greatest combination (e.g., average) of association scores of connections between the start "dental caries" node, through the intermediate nodes, to the first terminal "compound" node. The computer system can then calculate a composite association score for the first compound and dental caries, such as based on an average association score of the connections along the shortest edge between the first terminal "compound" node and the start "dental caries" node, weighted (e.g., divided) by a number of intermediate nodes along this edge.

For example, the computer system can: identify the target node in the semantic network; define a radius limit for a distance from the target node to nodes in the target domain; and identify the subset of nodes, in the semantic network, in the target domain and within the radius limit of the target node in Block S142.

In another example, for a first node, in a subset of nodes, representing a first concept in the target domain, the computer system can identify a first population of edges, in the semantic network, connecting the target node and the first node. Next, for each edge in the first population of edges, the computer system can calculate an intermediate association score, in a first set of intermediate association scores, based on association scores and directions contained in connections between nodes along the edge in the semantic network, and then calculate a first composite association score for the first concept, in the target domain and represented by the first node, based on a first combination of the first set of intermediate association scores.

Similarly, the computer system can calculate a composite action characteristic for the first compound and dental caries, such as by multiplying all action characteristics of the connections along this shortest edge between the first terminal "compound" node and the start "dental caries" node.

The computer system can additionally or alternatively implement similar methods and techniques to: calculate a set of edges between the first terminal "compound" node and the start "dental caries" node; calculate composite association scores and composite action characteristics for these edges; identify a first subset of these edges that exhibit composite association scores greater than the threshold association score, such as described above; and flag or store this first subset of these edges to return to the user.

Yet alternatively, because one compound may effect "dental caries" along multiple unique pathways, the computer system can implement similar methods and techniques to calculate a set of discrete, contiguous edges between the first terminal "compound" node and the start "dental caries" node and calculate one composite association score and one composite action characteristic representing all of these discrete, contiguous edges between the first terminal "compound" node and the start "dental caries" node by: calculating a first average association score of the connections along a first edge between the first terminal "compound" node and the start "dental caries" node; dividing the first average association score by the quantity of nodes along a first edge to calculate a first normalized association score;

repeating this process for each other edge connecting the first terminal "compound" node and the start "dental caries" node; and calculating a sum of these normalized association scores.

The computer system can repeat this process for each other terminal "compound" node detected in the semantic network or otherwise linked to the start "dental caries" node.

The computer system then: rank these subsets of edges— between the terminal "compound" nodes and the start "dental caries" node—by association score; extracts compound descriptors for terminal nodes on these edges from the semantic network, such as including compound name and chemical composition; extracts identifiers of resources that informed connections between nodes along these edges from the semantic network; and presents a list of these compounds—and their descriptors, links to related resources, and composite action scores, etc.—ranked by composite association score in the user portal.

8.2 Secondary Computer System Hypothesis Assessment

In one variation, the computer system can generate hypotheses to assist a user validating a user-defined hypothesis once the user has entered the hypothesis query into the research portal. Similarly, the computer system can act as a secondary check for a user's predicted hypothesis.

Similar to the example described above, the user can enter a search query of "bacterium" into the research portal as a user-defined hypothesis for root cause and/or for a pathway for mitigating dental caries and therefore functions to focus discovery of compounds that may affect dental caries exclusively to bacterium-related pathways. Conversely, in this example, exclusion of the search term "bacterium" expands the user's search through the semantic network to include any pathway (e.g., bacteria, genetics, viruses, fungi) that may affect dental caries.

For example, in response to receiving a query for a user-defined hypothesis in the form of a target concept, "particular compound," and a target domain, "disease", at the research portal, the computer system can: scan the semantic network for disease concepts; identify a population of nodes, including disease concepts in the semantic network in Block S141; isolate a set of edges between nodes in a subset of nodes within a distance (e.g., n-dimensional distance) of the particular compound in Block S145; identify concepts along the set of edges in the semantic network; generate a hypothesis, in a set of hypotheses, for directions and magnitudes of effects of concepts on the target concept based on association scores and action characteristics stored in connections along the edge; and return the set of hypotheses, ranked by magnitude of effect, to the research portal in Block S160.

Therefore, the set of hypotheses can be reviewed by the user at the research portal and thereby, assist the user with assessing and/or validating their initial hypothesis of "bacterium" as a root cause and/or for a pathway for mitigating dental caries, queried at the research portal.

8.3 Action Pathway Discovery

Furthermore, in this example, once the user selects a particular compound from this list, the computer system can predict an action pathway between the compound and dental caries based on action characteristics associated with connections between nodes of a particular edge—in the semantic network—between "dental caries" and the particular compound.

For example, the computer system can: derive multiple edges between the particular compound and the "dental caries" node in the semantic network; calculate a composite association score for each of these edges; sort these edges by association score; and presents the particular compound to the user with multiple possible action pathways sorted by composite association score.

Additionally or alternatively, the computer system can: generate a visualization depicting these edges, including the "dental caries" start node, the terminal node for this particular compound, and nodes along these edges; and label edges in this visualization with their corresponding composite association scores.

Once the user selects a particular action pathway from this list or visualization, the computer system can derive a description of a possible action pathway for the particular compound effecting dental caries. In one example, the particular action pathway selected by the user corresponds to an edge containing an intermediate node representing a particular bacterium and directly connecting the "dental caries" start node and the terminal node for this particular compound in the semantic network. In this example, if the composite action characteristic between the terminal node for this particular compound and the intermediate "bacterium" node is negative, the computer system can predict an inverse correlation between the particular compound and the particular bacterium (e.g., the compound reduces frequency of the particular bacterium). Similarly, if a composite action characteristic between the intermediate "bacterium" node and the "dental caries" start node is positive, the computer system can predict a direct correlation between the particular bacterium and dental caries (e.g., that the particular bacterium promotes dental caries). Accordingly, the computer system can generate a prediction for the action pathway for this compound, including "the [particular compound] suppresses the [particular bacterium], which reduces dental caries." The computer system can then return this prediction to the user, such as in the form of a textual statement or by annotating connections—between nodes along this edge of the semantic network—represented in the visualization within elements of this action pathway prediction statement.

In another example, the particular action pathway selected by the user corresponds to an edge containing: a first intermediate node representing a particular gene and directly connected to the terminal node for this particular compound in the semantic network; and a second intermediate node representing a particular bacterium and connecting the first intermediate node and the "dental caries" start node in the semantic network. In this example, if a first composite action characteristic between the terminal compound node for this particular compound and the first intermediate "gene" node is positive, the computer system can predict a direct correlation between the particular compound and the particular gene (e.g., the compound upregulates the particular gene). Similarly, if a second action characteristic between the first intermediate "gene" node and the second intermediate "bacterium" node is positive, the computer system can predict a direct correlation between the gene and the particular bacterium (e.g., expression of the gene promotes the particular bacterium). Furthermore, if a third action characteristic between the second intermediate "bacterium" node and the start "dental caries" node is negative, the computer system can predict an inverse correlation between the particular bacterium and dental caries (e.g., presence of the bacterium suppresses dental caries). Accordingly, the computer system can generate a prediction for the action pathway for this compound, including "the [particular compound] upregulates the [particular gene], which promotes the [particular bacterium], which reduces "dental caries." The computer system can then return this prediction to the user.

For example, the computer system can include a reasoning module (or "language model") configured to transform edges between nodes in the semantic network back into a natural language (or visual) description of the predicted mechanism of an action pathway selected by or presented to the user.

8.4 Inferences of Nearby Compounds

In one variation, the computer system can execute Blocks of the method S100 to generate a list of compounds directly connected to "dental caries." Once a user has selected a particular compound from this list of compounds, at the research portal, the computer system can generate inferences (or "hypotheses") of other nearby compounds that produce similar effects.

For example, the user enters a query that includes "fluoride" into the research portal. Accordingly, the computer system can implement methods and techniques similar to those described above to retrieve a set of nearby compounds in the semantic network that provide similar effects of "fluoride" on "dental caries". In this example, if the action characteristic is negative (e.g., "prevents") between the particular compound "fluoride" and the particular disease "dental caries," the computer system can: predict that the particular compound, "fluoride," is beneficial and prevents "dental caries"; scan the semantic network for other nearby compounds, according to a compound threshold (e.g., ten closest compounds); identify a subset of compounds that produce the similar effect of prevention of "dental caries" as the particular compound, "fluoride;" predict that the subset of compounds are also beneficial and prevent "dental caries;" generate a set of hypotheses, based on the predictions of the particular compound and the subset of compounds; and present these hypotheses of compounds nearby "fluoride" that prevent "dental caries" within the research portal for the user.

Additionally or alternatively, the computer system can implement methods and techniques described above to generate a list of side effects associated with "fluoride." The computer system can then access this list of side effects associated with "fluoride" and detect novel compounds (indirectly connected) that produce similar side effects.

For example, in response to the list of side effects for "fluoride" corresponding to positive action characteristics (e.g., causes, increases) that are connected to other secondary disease concepts (e.g., tooth discoloration, tooth decay, high blood pressure, seizures, osteosarcoma, nausea) in the semantic network, the computer system can: scan the semantic network for compound concepts that are indirectly connected to these secondary disease concepts; identify a subset of compounds that produce the similar effects of the particular compound, "fluoride" on these secondary disease concepts; predict that the subset of compounds are also disadvantageous and cause these secondary disease concepts; generate a set of hypotheses, based on the predictions of the particular compound and the subset of compounds; and present these hypotheses of compounds that produce the same effects as "fluoride" on these secondary disease concepts, (e.g., causes "dental caries") within the research portal for the user.

Therefore, the computer system can generate a hypothesis of predicted effects of fluoride on "dental caries" and can also generate a set of hypotheses of compounds that produce the same effects as "fluoride" to the research portal for presentation to the user to inform the user's research.

9. Action Pathways: Discovery+Delivery

In one implementation, the computer system can implement the methods and techniques described above to derive possible action pathways between concepts searched or selected by the user based on secondary concepts contained in intermediate nodes along edges in the semantic network extending between these nodes.

However, in this implementation, the computer system can extract data from the semantic network related to gustatory sensation (or "taste perception") and flavor profiles of concepts (e.g., food product, waste product, compounds) including taste qualities (e.g., bitterness, sweetness, saltiness, sourness, umami) that are connected to taste chemicals (e.g., tastants) of consumable substances (e.g., food, beverages) informed by the corpus of scientific publications. More specifically, flavor profiles represent the compounds, taste qualities, and ingredients found in consumable substances that can be detected upon consumption by a user (e.g., delivery to a user). The computer system can derive action pathways between these taste qualities and the concepts searched or selected by the user.

Accordingly, the computer system can present these action pathways to the user, thereby enabling the user to gain further insight into how a concept can directly or indirectly affect another concept and how the concept may be perceived by the user upon consumption, based on taste qualities that are directly or indirectly connected to the concept.

9.1 Delivery: Flavor Profile+Taste Qualities

Generally, the computer system can generate predictions, generate hypotheses, or return lists of related concepts labeled with taste qualities that affect a target concept.

In one variation, the user can enter a query that includes "dental caries AND bioactive compounds" into the user portal. Accordingly, the computer system can implement the methods and techniques described above to generate a list of bioactive compounds associated with "dental caries" (e.g., characterized by direct or indirect association scores with "dental caries" greater than the threshold association score). The computer system can then isolate edges connecting a bioactive compound node and a taste quality node—such as a sourness node or a bitterness node—and return a list of bioactive compound concepts labeled with taste qualities that affect "dental caries."

For example, the computer system can: receive a selection for the target concept including a target disease at the research portal in Block S140; receive a selection for the target domain including bioactive compounds at the research portal in Block S140; and then generate a set of hypotheses to isolate the set of edges, in the semantic network, between the target node representing the target disease and the subset of nodes labeled as bioactive compounds and for each node, in a subset of nodes, labeled with a bioactive compound concept, isolate a set of edges coupling the node to the target concept in Block S145, calculate a composite association score between the bioactive compound concept and the target disease based on a combination of association scores and directions contained in the set of edges in Block S146, isolate a second set of edges coupling the node to a nearest secondary node, in the semantic network, labeled with a taste quality in Block S148, and calculate a taste association score for the bioactive compound concept based on a second combination of association scores contained in the second set of edges in Block S149. Then the computer system can: compile a first list of the set of bioactive compound concepts ranked by composite association score in Block S150; and render the first list of the set of bioactive compound concepts, labeled with taste qualities and taste association scores, within the research portal to the user in Block S160.

In another variation, the user can enter a query that includes a target disease and a target domain (e.g., bioactive compound concepts) into the user portal. Accordingly, the computer system can execute Blocks of the method S100 to generate a list of bioactive compounds associated with the target disease and/or generate a hypothesis between a taste quality and the target disease.

For example, the computer system can receive selection for the target concept including a target disease and for the target domain including bioactive compound concepts at the research portal and isolate the initial set of edges in the semantic network, between the target node representing the target disease and the subset of nodes labeled with bioactive compound concepts; calculate the composite association score between the target disease and the bioactive compound concept based on a combination of association scores and directions contained in the first set of edges; calculate the taste association score between the taste quality and the bioactive compound concept based on a second combination of association scores and directions contained in the second set of edges; and generate a first hypothesis, in a set of hypotheses, for a direction and a magnitude of an effect of the taste quality on the target disease based on the composite association score and the taste association score. The computer system can return the set of hypotheses, ranked by magnitude of effect, to the research portal and/or compile a first list of bioactive compound concepts connected to the target disease, labeled with taste qualities and taste association scores, and ranked by composite association score; and render the first list of bioactive compound concepts for presentation within the research portal to the user.

Later, the computer system can receive selection of a first taste quality including sweetness and a taste association score threshold at the research portal; extract a subset of bioactive compound concepts, labeled with sweetness, from the first list of bioactive compound concepts; and scan the subset of bioactive compound concepts, labeled with sweetness, for taste association scores. Then, in response to the taste association scores exceeding the taste association score threshold, the computer system can: compile the subset of bioactive compound concepts, labeled with sweetness and taste association scores, into a second list of bioactive compound concepts ranked by taste association score; and render the second list of bioactive compound concepts for presentation within the research portal to the user.

In yet another variation, the user can enter a query that includes a target concept (e.g., waste product) and a target domain (e.g., bioactive compound concepts) into the user portal. Accordingly, the computer system can execute Blocks of the method S100 to generate a list of bioactive compounds associated with the waste product labeled with taste qualities and taste association scores.

For example, the computer system can: receive selection for the target concept including a waste product and for the target domain including bioactive compound concepts at the research portal; isolate the initial set of edges, in the semantic network, between the target node representing the waste product and the subset of nodes labeled with bioactive compound concepts; calculate the composite association score between the waste product and the bioactive compound concept node based on a combination of association scores and action characteristics contained in the first set of edges; calculate the taste association score between the taste quality and the bioactive compound concept node based on a second combination of association scores and action characteristics contained in the second set of edges; compile a first list of bioactive compound concepts connected to the waste product, labeled with taste qualities and taste association scores, and ranked by composite association score; and render the first list of bioactive compound concepts for presentation within the research portal to the user.

9.2 Discovery+Delivery: Multi-Pathway Secondary Concepts

Generally, the computer system can derive possible action pathways between concepts separated by a threshold quantity of intermediate nodes (e.g., 5, 10, 40), which store secondary concepts along edges in the semantic network. More specifically, the computer system can isolate edges in the semantic network connecting the target node to intermediate nodes, labeled with the target domain, separated by fewer than a threshold quantity of intermediate nodes in the semantic network.

In one variation, the computer system can execute Blocks of the method S100 to derive action pathways between a waste product concept, secondary concepts including bioactive compounds, and the target domain including disease concepts to generate hypotheses, which can inform the user's research for consumption of edible food waste products.

For example, the computer system can receive selection for the target concept including a waste product at the research portal and for the target domain including disease concepts at the research portal and receive selection for a domain for intermediate nodes including bioactive compound concepts at the research portal. Then, for a first node, in the subset of nodes, representing a first disease concept in the target domain, the computer system can identify a first population of edges, in the semantic network, connecting the target node representing the waste product and the first node representing the first disease concept and for each edge in the first population of edges, the computer system can calculate an intermediate association score, in a first set of intermediate association scores, based on association scores and directions contained in connections between intermediate nodes, representing bioactive compound concepts, along the edge in the semantic network. The computer system can: calculate a first composite association score for the first disease concept, in the target domain and represented by the first node, based on a first combination of the first set of intermediate association scores; generate a second hypothesis, in the set of hypotheses, for a direction and a magnitude of an effect of the bioactive compound concepts on the first disease concept based on intermediate association scores and the first composite association score; and return the set of hypotheses, ranked by magnitude of effect, to the research portal.

Additionally, the computer system can compile a first list of bioactive compound concepts ranked by composite association score and render the first list of bioactive compound concepts within the research portal for presentation to the user. Then, in response to receiving selection of a first bioactive compound concept from the first list of bioactive compound concepts, the computer system can: generate a third hypothesis, in the set of hypotheses, for a direction and a magnitude of an effect of the first bioactive compound concept on the first disease concept; and render the third hypothesis within the research portal for the user.

Similarly, in another variation, the computer system can execute Blocks of the method S100 to derive action pathways between a food product concept, secondary concepts including bioactive compounds, and the target domain including disease concepts to generate hypotheses, which can inform the user's research for consumption of the food product.

For example, the computer system can: receive selection for the target concept including a food product and for the target domain including disease concepts at the research portal; isolate the first set of edges, in the semantic network, between the target node representing the food product and the set of nodes labeled with disease concepts; calculate a first set of composite association scores between the food product and the set of nodes labeled with disease concepts based on the first combination of the first set of intermediate association scores; isolate the second set of edges between intermediate nodes representing bioactive compound concepts along the first set of edges to the set of nearest secondary nodes, labeled with taste qualities; and calculate the taste association score between the taste quality and the intermediate node representing a bioactive compound concept based on the second combination of association scores and directions stored in connections along the edge; and generate a second hypothesis, in the set of hypotheses, for a direction and a magnitude of an effect of the bioactive compound concepts on the disease concepts based on intermediate association scores and the first composite association score.

Furthermore, the computer system can compile a first list of bioactive compound concepts, ranked by magnitude of effect; render the first list of bioactive compound concepts within the research portal to the user; receive selection of a first taste quality including bitterness at the research portal; extract a subset of bioactive compound concepts, labeled with bitterness, from the first list of bioactive compound concepts; and generate a third hypothesis, in the set of hypotheses, for a direction and a magnitude of an effect of bitterness on the food product based on association scores and directions stored in connections along the second set of edges.

Additionally or alternatively, in response to receiving selection for removal of the first taste quality including bitterness at the research portal, the computer system can generate a fourth hypothesis, in the set of hypotheses, for a direction and a magnitude of an effect of the bioactive compound concepts on the disease concepts based on composite association scores and taste association scores.

Therefore, the computer system can generate hypotheses of how an intermediate node concept related to the target concept has an effect on a concept in the target domain or compile and render a list of these concepts, ranked by magnitude of effect. The computer system can also derive action pathways between concepts connected to secondary concepts stored in intermediate nodes, thereby informing a user's research about intermediate concepts (e.g., waste products, food products, taste qualities, bioactive compounds, diseases) in relation to concepts queried and selected by the user.

9.3 Inferences of Nearby Taste Qualities

In one variation, the computer system can execute Blocks of the method S100, similar to the methods and techniques described above regarding inferences of compounds, to scan the semantic network for taste qualities directly connected to a target concept (e.g., target bioactive compound) and generate hypotheses based on other nearby nodes labeled with the domain of the target concept (e.g., bioactive compound concepts).

More specifically, if the computer system detects that the target bioactive compound is not directly connected to any taste qualities, the computer system can generate hypotheses for the target bioactive compound based on other nearby bioactive compound nodes proximal to the target bioactive compound—such as within a radius limit defining a distance from the target bioactive compound node to other bioactive compound nodes—that are directly connected to taste qualities.

For example, the computer system can receive selection for the target concept including a target bioactive compound and for the target domain including taste qualities at the research portal and scan the semantic network for taste qualities connected to the bioactive compound. Then, in response to detecting absence of a taste quality connected to the bioactive compound, the computer system can isolate a set of bioactive compound nodes, in the semantic network, proximal the target bioactive compound and for each bioactive compound node in the set of bioactive compound nodes, the computer system can: isolate a third set of edges coupling the bioactive compound node to the target bioactive compound; calculate a second composite association score between the bioactive compound node and the target bioactive compound based on a third combination of association scores and directions contained in the set of edges; isolate a fourth set of edges, in the semantic network, coupling the bioactive compound node to a nearest secondary node, in the semantic network, labeled with the taste quality; calculate a second taste association score between the taste quality and the bioactive compound node based on a fourth combination of association scores contained in the fourth set of edges; and generate a second hypothesis, in the set of hypotheses, for the direction and the magnitude of the effect of the taste quality on the target bioactive compound based on taste association scores and action characteristics stored in connections along the fourth set of edges.

Therefore, the computer system can generate hypotheses of taste qualities for a target concept that is indirectly connected to a taste quality by interpolating taste quality connections of other nearby nodes labeled with the domain of the target concept.

10. Secondary Concepts

In one variation, the computer system can implement the methods and techniques describe above to generate a list of secondary disease concepts that represent side effects of a particular compound.

In the foregoing example, the computer system can generate a list of side effects for a particular compound, "fluoride," which corresponds to action characteristics (e.g., causes, increases, induces), in the form of directional keywords from the corpus of resources. These action characteristics can also be connected to secondary disease concepts (e.g., tooth discoloration, tooth decay, high blood pressure, seizures, osteosarcoma, nausea) in the semantic network.

For example, the computer system can receive selection for a target concept including a target compound at the research portal in Block S140, receive selection for a target domain including disease concepts at the research portal in Block S140, and then generate a set of hypotheses to: scan the semantic network for disease concepts; isolate a set of disease nodes, in the semantic network, nearest the target concept representing the target compound in Block S144; for each disease node in the set of disease nodes, isolate a set of edges coupling the disease node to the target concept in Block S145, calculate a composite association score between the disease node and the target concept based on a combination of association scores and directions contained in the set of edges in Block S146, isolate a secondary set of edges coupling the disease node to the target concept, and calculate a secondary composite association score between the disease node and the target concept based on a secondary combination of association scores and directions contained in the secondary set of edges in Block S147. Then, the computer system can: compile a first list of disease concepts contained in the set of disease nodes, ranked by secondary composite association score in Block S150; and present the first list of disease concepts labeled as side effects of the target concept, representing the target compound, within the research portal to the user in Block S160. Furthermore, the computer system can implement methods and techniques described below to render a natural language script of the disease concepts as side effects within the research portal for the user in Block S151. Thus, the computer system can present a list of disease concepts representing possible side effects (e.g., tooth discoloration, tooth decay, high blood pressure, seizures, osteosarcoma, nausea) of the particular compound, "fluoride," selected by the user.

Additionally or alternatively, the computer system can implement similar methods and techniques to generate a list of secondary disease concepts that represent symptoms of a consumable substance (e.g., food product, waste product, food ingredients).

For example, the computer system can receive selection for the target concept including a food product and, for the target domain including disease concepts at the research portal, then the computer system can generate the set of hypotheses, in which the computer system can: scan the semantic network for disease concepts; and isolate a set of disease nodes, in the semantic network, nearest the target concept representing the food product. Then, for each disease node in the set of disease nodes, the computer system can: isolate a first set of edges coupling the disease node to the food product; calculate a composite association score between the disease node and the food product based on a combination of association scores and directions contained in the first set of edges; isolate a secondary set of edges coupling the disease node to the food product; and calculate a secondary composite association score between the disease node and the food product based on a secondary combination of association scores and directions contained in the secondary set of edges. The computer system can compile a first list of disease concepts contained in the set of disease nodes, ranked by secondary composite association score; and present the first list of disease concepts labeled as symptoms of the food product, within the research portal to the user.

Therefore, the computer system can present a list of disease concepts stored in disease nodes which represent possible symptoms of diseases of the food product (e.g., healthy cookie, protein bar, chewable tablet, etc.) selected by the user. The computer system can also generate a natural language script of these secondary disease concepts according to a language model, as described below.

11. Language Model

In one implementation, the computer system can include a reasoning module (or "language model") configured to:

transform edges between nodes in the semantic network back into a natural language (or visual) description of the predicted mechanism of an action pathway selected by or presented to the user; transform predicted hypotheses into natural language descriptions; and transform lists of concepts into natural language descriptions.

In one variation, the computer system can automatically search for other diseases nearby the particular compound selected by the user in the semantic network to find correlations between the particular compound and the nearby diseases.

Additionally or alternatively, the computer system can automatically search for other compounds nearby the particular disease selected by the user in the semantic network to find correlations between the particular disease and the nearby compounds. More specifically, the computer system can generate a list of correlations of concepts based on a direct documentation status (e.g., found in literature), and/or based on an indirect (or "novel") documentation status (e.g., found in patient medical records rather than peer-reviewed literature), to predict the correlation between the particular disease and nearby compounds.

For example, the user enters a query that includes "dental caries AND compound" into the user portal. Accordingly, the computer system implements methods and techniques similar to those described above to retrieve a set of compounds connected to "dental caries" (e.g., characterized by direct or indirect association scores with "dental caries" greater than the threshold association score). The computer system can detect an individual compound in the set of compounds and predict, based on correlations between the concepts, that this compound downregulates a bacterium which then reduces "dental caries". However, the computer system can also predict that this compound kills gut bacteria and causes liver failure. The computer system can apply the language model to these hypotheses and return human readable natural language text descriptions in the form of: "the [particular compound] downregulates the [particular bacterium], which reduces [particular disease], which kills [secondary bacterium], which causes [secondary disease]."

Therefore, the computer system can: automatically extract nearby concepts (e.g., compound, bacterium, taste perception, germ etc.) from the semantic network; generate hypotheses based on likelihood of correlation between the user selected concept and nearby concepts; and translate these hypotheses into natural language descriptions, according to a language model, to return human-readable results and predictions within the research portal.

11.1 Language Model Example

In one variation, the computer system can execute Blocks of the method S100 to generate a set of hypotheses and can transform these hypotheses into natural language descriptions for the user to understand.

For example, the computer system can generate a set of hypotheses: identify a first sequence of nodes along a first edge, in a set of edges, connecting a first concept in the target domain to a target concept in the semantic network; extract a first sequence of chemical and biological concepts from the first sequence of nodes; extract a first set of association scores and a first set of action characteristics stored in a first series of connections between the first sequence of nodes along the first edge; derive a first direction of a first effect of the first concept on the target concept based on a first combination of the first set of action characteristics; derive a first magnitude of the first effect, in the first direction, based on a second combination of the first set of association scores; and compile the first direction and the first magnitude into a first hypothesis for the first effect of the first concept on the target concept.

Then, the computer system can: initialize a first natural language script; insert a first sequence of words, representing the first sequence of chemical and biological concepts, into the first natural language script; transform the first set of action characteristics into a second set of words in Block S151; insert the second set of words, interposed between the first sequence of words, in the first natural language script according to a language model; populate the first natural language script with the first magnitude and the first effect; and render the first natural language script, describing the first hypothesis in natural language, within the research portal in Block S160.

The computer system can also implement similar methods and techniques to transform edges between nodes in the semantic network into a natural language description of the predicted mechanism of an action pathway selected by or presented to the user and/or to transform lists of concepts into natural language descriptions according to the language model.

However, the computer system can implement this process or any other methods or techniques to derive hypotheses for associations, action characteristics, taste qualities, and action pathways between concepts based on edges that connect nodes matching search terms entered by the user; and the computer system can present these hypotheses to the user in any other way.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for automated therapy discovery comprising:
   accessing a corpus of scientific publications;
   compiling a population of semantic concepts represented in the corpus of scientific publications into a vector space model based on:
      proximity of semantic concepts within individual scientific publications, in the corpus of scientific publications; and
   frequency of semantic concepts across the corpus of scientific publications;
   deriving domains of a set of chemical and biological concepts in the vector space model based on proximity to domain descriptors in the vector space model;
   deriving association scores between connected chemical and biological concepts, in the set of chemical and biological concepts, based on proximity in the vector space model;
   deriving action characteristics between connected chemical and biological concepts, in the set of chemical and biological concepts, based on action descriptors in the vector space model;
   generating a semantic network comprising:
      a set of nodes representing the set of chemical and biological concepts labeled with domains; and
      connections between nodes storing association scores and action characteristics;
   receiving a query for a target concept and a target domain at a research portal;
   generating a set of hypotheses by:
      isolating a set of edges, in the semantic network, between a target node representing the target concept and a subset of nodes labeled with the target domain;
      for each edge in the set of edges in the semantic network:
         identifying a subset of chemical and biological concepts along the edge in the semantic network; and
         generating a hypothesis, in a set of hypotheses, for a direction and a magnitude of an effect of the subset of chemical and biological concepts on the target concept based on association scores and action characteristics stored in connections along the edge; and
   returning the set of hypotheses, ranked by magnitude of effect, to the research portal.

2. The method of claim 1, further comprising, for a first node, in the subset of nodes, representing a first concept in the target domain:
   identifying a first population of edges, in the semantic network, connecting the target node and the first node;
   for each edge in the first population of edges:
      calculating an intermediate association score, in a first set of intermediate association scores, based on association scores and directions contained in connections between nodes along the edge in the semantic network; and
   calculating a first composite association score for the first concept, in the target domain and represented by the first node, based on a first combination of the first set of intermediate association scores.

3. The method of claim 1, wherein generating the set of hypotheses comprises:
   identifying the target node in the semantic network;
   defining a radius limit for a distance from the target node to nodes in the target domain; and
   identifying the subset of nodes, in the semantic network, in the target domain and within the radius limit of the target node.

4. The method of claim 1, wherein isolating the set of edges in the semantic network comprises isolating the set of edges in the semantic network connecting the target node to nodes, labeled with the target domain, separated by fewer than a threshold quantity of intermediate nodes in the semantic network.

5. The method of claim 1, further comprising:

projecting sets of edges, in the semantic network, between the target node and the subset of nodes onto a virtual surface to generate a visualization of a region of the semantic network representing connections between the target concept and the target domain;

labeling edges, represented in the visualization, within concepts extracted from nodes between the target node and the subset of nodes in the semantic network; and rendering the visualization within the research portal for the user.

6. The method of claim 1:

wherein receiving the query for the target concept and the target domain at the research portal comprises:

receiving selection for the target concept comprising a target compound at the research portal; and receiving selection for the target domain comprising disease concepts at the research portal;

wherein generating the set of hypotheses comprises:

scanning the semantic network for disease concepts;

isolating a set of disease nodes, in the semantic network, nearest the target concept representing the target compound;

for each disease node in the set of disease nodes:

isolating a first set of edges coupling the disease node to the target concept;

calculating a composite association score between the disease node and the target concept based on a combination of association scores and directions contained in the set of edges;

isolating a secondary set of edges coupling the disease node to the target concept; and calculating a secondary composite association score between the disease node and the target concept based on a secondary combination of association scores and directions contained in the secondary set of edges; and wherein returning the set of hypotheses to the research portal comprises:

compiling a first list of disease concepts contained in the set of disease nodes, ranked by secondary composite association score; and presenting the first list of disease concepts labeled as side effects of the target compound, within the research portal to the user.

7. The method of claim 1:

wherein receiving the query for the target concept and the target domain at the research portal comprises:

receiving selection for the target concept comprising a target disease at the research portal; and receiving selection for the target domain comprising bioactive compounds at the research portal;

wherein generating the set of hypotheses comprises:

isolating the set of edges, in the semantic network, between the target node representing the target disease and the subset of nodes labeled as bioactive compounds; and for each node, in the subset of nodes, labeled with a bioactive compound concept:

isolating a first set of edges coupling the node to the target concept;

calculating a composite association score between the bioactive compound concept and the target disease based on a combination of association scores and directions contained in the first set of edges;

isolating a second set of edges coupling the node to a nearest secondary node, in the semantic network, labeled with a taste quality; and calculating a taste association score for the bioactive compound concept based on a second combination of association scores contained in the second set of edges; and wherein returning the set of hypotheses to the research portal comprises:

compiling a first list of the set of bioactive compound concepts ranked by composite association score; and rendering the first list of the set of bioactive compound concepts, labeled with taste qualities and taste association scores, within the research portal to the user.

8. The method of claim 1:

wherein receiving the query for the target concept and the target domain at the research portal comprises:

receiving selection for the target concept comprising a target disease at the research portal; and receiving selection for the target domain comprising compound concepts at the research portal;

wherein generating the set of hypotheses comprises:

isolating the set of edges, in the semantic network, between the target node representing the target disease and the subset of nodes labeled as compound concepts; and for each node, in the subset of nodes, labeled with a compound concept:

isolating a first set of edges coupling the node to the target concept; and calculating a composite association score between the compound concept and the target concept based on a combination of association scores and directions contained in the first set of edges; and wherein returning the set of hypotheses to the research portal comprises:

compiling a first list of compound concepts, ranked by composite association score; and rendering the first list of compound concepts for presentation within the research portal to the user.

9. The method of claim 8, further comprising, in response to selection of a high association strength filter from the research portal:

accessing a first definition of high association strength;

identifying a first subset of compound concepts, from the first list of compound concepts, exhibiting high association strength based on the first definition of high association strength;

compiling the first subset of compound concepts into a second list of compound concepts ranked by composite association score and labeled with high association strength; and rendering the second list of compound concepts within the research portal for the user.

10. The method of claim 1:

wherein receiving the query for the target concept and the target domain at the research portal comprises:

receiving selection for the target concept comprising a target disease at the research portal; and receiving selection for the target domain comprising bacteria concepts at the research portal;

wherein generating the set of hypotheses comprises:

isolating the set of edges, in the semantic network, between the target node representing the target disease and the subset of nodes labeled as bacteria concepts; and for each node, in the subset of nodes, labeled with a bacterium concept:

isolating a first set of edges coupling the node to the target concept; and calculating a composite association score between the bacterium concept and the target disease based on a combination of association scores and directions contained in the set of edges; and wherein returning the set of hypotheses to the research portal comprises:

compiling a first list of bacteria concepts, ranked by composite association score; and rendering the first list of bacteria concepts for presentation within the research portal to the user.

11. The method of claim 1, wherein deriving action characteristics between connected chemical and biological concepts, in the set of chemical and biological concepts, based on action descriptors in the vector space model comprises:

deriving action characteristics representing directions of correlations between connected chemical and biological concepts based on the presence of directional keywords between chemical and biological concepts within individual scientific publications of the corpus of scientific publications.

12. The method of claim 11, wherein deriving action characteristics comprises deriving action characteristics representing directions of correlations between connected chemical and biological concepts based on the presence of directional keywords, directional keywords is selected from the group consisting essentially of:

upregulates;

downregulates;

catalyzes;

inhibits;

starts;

stops;

causes;

prevents;

promotes;

demotes;

grows;

kills;

induces; and reduces.

13. The method of claim 1, wherein generating the set of hypotheses comprises:

identifying a first sequence of nodes along a first edge, in the set of edges, connecting a first concept in the target domain to the target concept in the semantic network;

extracting a first sequence of chemical and biological concepts from the first sequence of nodes;

extracting a first set of association scores and a first set of action characteristics stored in a first series of connections between the first sequence of nodes along the first edge;

deriving a first direction of a first effect of the first concept on the target concept based a first combination of the first set of action characteristics;

deriving a first magnitude of the first effect, in the first direction, based on a second combination of the first set of association scores; and compiling the first direction and the first magnitude into a first hypothesis for the first effect of the first concept on the target concept.

14. The method of claim 13, further comprising:

initializing a first natural language script;

inserting a first sequence of words, representing the first sequence of chemical and biological concepts, into the first natural language script;

transforming the first set of action characteristics into a second set of words;

inserting the second set of words, interposed between the first sequence of words, in the first natural language script according to a language model;

populating the first natural language script with the first magnitude and the first effect; and rendering the first natural language script, describing the first hypothesis in natural language, within the research portal.

15. A method for automated therapy discovery comprising:

accessing a corpus of scientific publications;

compiling a population of semantic concepts represented in the corpus of scientific publications into a vector space model;

deriving domains of a set of chemical and biological concepts in the vector space model based on proximity to domain descriptors in the vector space model;

deriving association scores between connected chemical and biological concepts, in the set of chemical and biological concepts, based on proximity in the vector space model;

deriving action characteristics between connected chemical and biological concepts, in the set of chemical and biological concepts, based on action descriptors in the vector space model;

generating a semantic network;

receiving a query for a target concept and a target domain at a research portal;

identifying a target node representing the target concept and a subset of nodes labeled with the target domain in the semantic network;

generating a set of hypotheses by:

identifying a subset of biological and chemical concepts in the target domain nearest the target concept;

for each concept in the subset of biological and chemical concepts:

isolating a set of edges coupling the concept to the target concept;

calculating a composite association score between the concept and the target concept based on a combination of association scores and directions contained in the set of edges; and generating a hypothesis, in a set of hypotheses, for a direction and a magnitude of an effect of the concept on the target concept based on association scores and action characteristics stored in connections along the set of edges; and rendering a first list of concepts, ranked by association score and linked to the set of hypotheses, for presentation within the research portal for the user.

16. The method of claim 15, further comprising, in response to selection of a first concept in the first list of biological and chemical concepts:

rendering a first hypothesis, in the set of hypotheses, within the research portal; and rendering a first natural language script, describing the first hypothesis in natural language, within the research portal.

17. The method of claim 15, further comprising:

projecting sets of edges, in the semantic network, between the target node and the subset of nodes onto a virtual surface to generate a visualization of a region of the semantic network representing connections between the target concept and the target domain;

labeling edges, represented in the visualization, with concepts extracted from nodes between the target node and the subset of nodes in the semantic network; and rendering the visualization within the research portal for the user.

18. The method of claim 15, further comprising, in response to selection for a direct documentation status filter at the research portal:

extracting a first subset of biological and chemical concepts from the list of biological and chemical concepts, exhibiting a direct documentation status;

compiling the first subset of biological and chemical concepts into a second list of biological and chemical concepts according to the direct documentation status filter; and rendering the second list of biological and chemical concepts, labeled with direct documentation statuses, within the research portal for the user to review.

19. The method of claim 15, further comprising:

in response to selection of a first publication date threshold at the research portal:

identifying a first subset of scientific publications in the corpus of scientific publications exceeding the first publication date threshold; and extracting a first cluster of identifiers from the semantic network corresponding to the first subset of scientific publications;

in response to selection of a second publication date threshold from the research portal:

identifying a second subset of scientific publications in the corpus of scientific publications falling below the second publication date threshold; and extracting a second cluster of identifiers from the semantic network corresponding to the second subset of scientific publications;

generating a second list of concepts ranked by publication date and labeled with the first cluster of identifiers and the second cluster of identifiers; and

presenting the second list of concepts, labeled with the first cluster of identifiers and the second cluster of identifiers, within the research portal for the user.

20. A method for automated therapy discovery comprising:

accessing a corpus of scientific publications;

compiling a population of semantic concepts represented in the corpus of scientific publications into a vector space model based on:

proximity of semantic concepts within individual scientific publications, in the corpus of scientific publications; and frequency of semantic concepts across the corpus of scientific publications;

deriving domains of a set of concepts in the vector space model based on proximity to domain descriptors in the vector space model;

deriving association scores between connected concepts, in the set of concepts, based on proximity in the vector space model;

deriving action characteristics between connected concepts, in the set of concepts, based on action descriptors in the vector space model;

generating a semantic network;

receiving a query for a target concept and a target domain at a research portal;

isolating a set of edges, in the semantic network, between a target node representing the target concept and a subset of nodes labeled with the target domain;

identifying a subset of concepts along each edge of the set of edges in the semantic network;

generating a hypothesis, in a set of hypotheses, for a direction and a magnitude of an effect of the subset of concepts on the target concept based on association scores and action characteristics stored in connections along each edge of the set of edges; and returning the set of hypotheses, ranked by magnitude of effect, to the research portal.

* * * * *